(12) United States Patent
Bermann et al.

(10) Patent No.: US 9,108,898 B2
(45) Date of Patent: Aug. 18, 2015

(54) CONTINUOUS METHOD FOR PRODUCING PRIMARY ALIPHATIC AMINES FROM ALDEHYDES

(71) Applicant: Oxea GmbH, Oberhausen (DE)

(72) Inventors: Dirk Bermann, Mülheim (DE); Matthias Eisenacher, Wesel (DE); Sebastian Geisel, Essen (DE); Leif Johnen, Voerde (DE); Peter Heymanns, Essen (DE); Norman Nowotny, Essen (DE); Kurt Schalapski, Oberhausen (DE); Heinz Strutz, Moers (DE)

(73) Assignee: OXEA GMBH, Oberhausen (DE)

( * ) Notice: Subject to any disclaimer, the term of this patent is extended or adjusted under 35 U.S.C. 154(b) by 0 days.

(21) Appl. No.: 14/415,193

(22) PCT Filed: Jul. 11, 2013

(86) PCT No.: PCT/EP2013/002069
§ 371 (c)(1),
(2) Date: Jan. 16, 2015

(87) PCT Pub. No.: WO2014/026726
PCT Pub. Date: Feb. 20, 2014

(65) Prior Publication Data
US 2015/0191415 A1    Jul. 9, 2015

(30) Foreign Application Priority Data
Aug. 17, 2012 (DE) .......................... 10 2012 016 433

(51) Int. Cl.
*C07C 209/26* (2006.01)
*C07C 209/52* (2006.01)
*C07C 249/02* (2006.01)

(52) U.S. Cl.
CPC ............. *C07C 209/26* (2013.01); *C07C 209/52* (2013.01); *C07C 249/02* (2013.01)

(58) Field of Classification Search
None
See application file for complete search history.

(56) References Cited

U.S. PATENT DOCUMENTS

| 8,664,444 | B2 | 3/2014 | Schalapski et al. |
| 2005/0107637 | A1 | 5/2005 | Gerlach et al. |

FOREIGN PATENT DOCUMENTS

| DE | 936211 | 12/1955 |
| DE | 19935448 A1 | 2/2001 |
| DE | 102010045142 A1 | 3/2012 |
| GB | 1421278 A | 1/1976 |
| WO | 9738955 A1 | 10/1997 |

OTHER PUBLICATIONS

Database CAPLUS in STN, Acc. No. 2007:733167, Martin et al., Chemie Ingenieur Technik (2007), 79(6), pp. 891-900 (abstract).*
International Preliminary Report on Patentability dated Feb. 26, 2015.
Houben-Weyl, Methoden der organischen Chemie, 4th edition, 1957, pp. 602-607, vol. XI/1, Georg Thieme Verlag, Stuttgart, Germany.
Handbook of Chemistry and Physics, 50th Edition, 1969, p. F-64, The Chemical Rubber Co., Cleveland.
International Search Report dated Sep. 23, 2013.
Chemie Ingenieur Technik (2007), 79(6), pp. 891-900.

* cited by examiner

*Primary Examiner* — Brian J Davis
(74) *Attorney, Agent, or Firm* — Michael W. Ferrell

(57) ABSTRACT

A continuous process for preparing primary aliphatic amines having 3 to 18 carbon atoms by reacting corresponding aliphatic aldehydes with ammonia and hydrogen in the presence of a hydrogenation catalyst, characterized in that the reaction is carried out without solvent at a molar ratio of aliphatic aldehyde to ammonia of more than 1 to 16, above the critical temperature and above the critical pressure of ammonia.

20 Claims, 1 Drawing Sheet

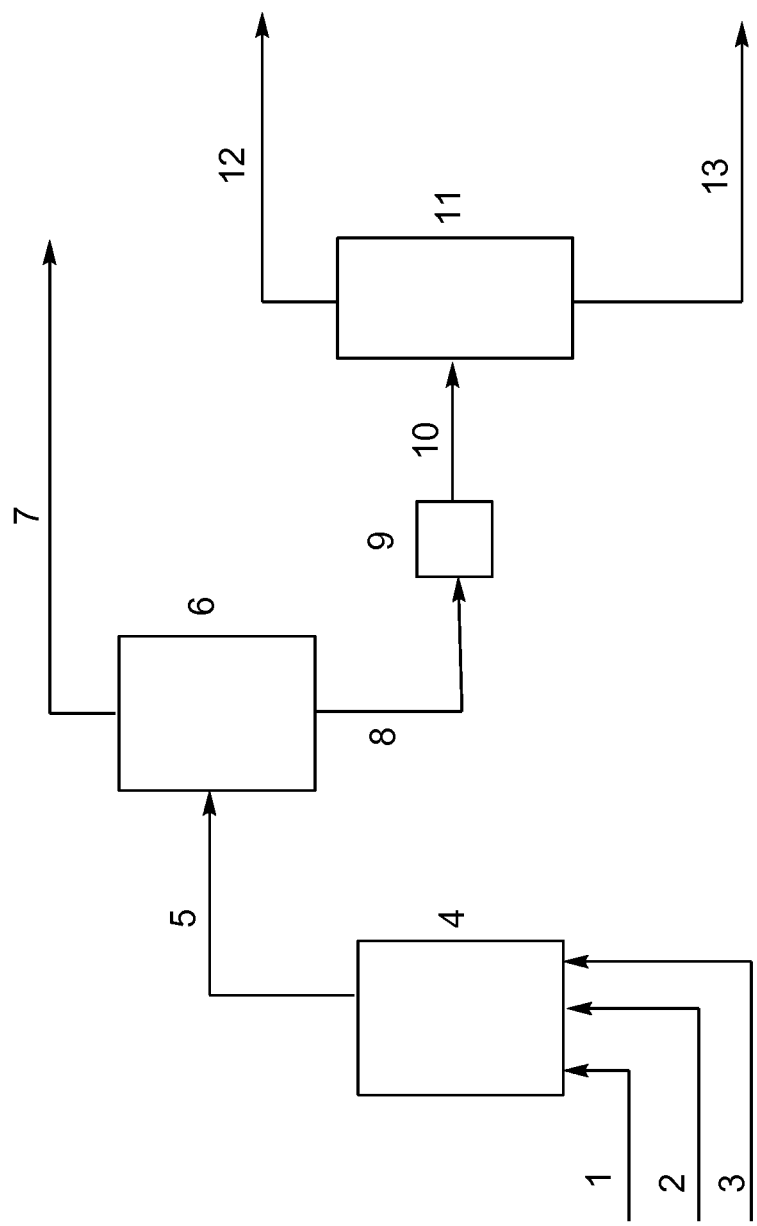

CONTINUOUS METHOD FOR PRODUCING PRIMARY ALIPHATIC AMINES FROM ALDEHYDES

CLAIM FOR PRIORITY

This application is a national phase application of PCT/EP2013/002069 FILED Jul. 11, 2013 which was based on application DE 10 2012 016 433.5 FILED Aug. 17, 2012. The priorities of PCT/EP2013/002069 and DE 10 2012 016 433.5 are hereby claimed and their disclosures incorporated herein by reference.

TECHNICAL FIELD

The present invention relates to a continuous process for preparing primary aliphatic amines having 3 to 18 carbon atoms by reductive amination of the corresponding aliphatic aldehyde with ammonia in the presence of a hydrogenation catalyst above the critical point of ammonia.

BACKGROUND

Aliphatic amines are important organic intermediates which are prepared on a large industrial scale. They are further processed for the preparation of agrochemicals or dyes for example, or they are used as additive in surface-active formulations, as a corrosion inhibitor in lubricants or as auxiliaries in the paper, textile and rubber industries.

The preparation of primary aliphatic amines from aldehydes and ammonia with hydrogen over a catalyst is known. This reaction is also referred to as reductive amination. The amine formation can be described by the following reaction stages:

  (1)

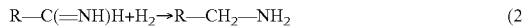  (2)

The first reaction stage initially eliminates water to produce an imine, which is then hydrogenated catalytically in a second reaction stage.

However, unwanted secondary reactions occur as the reaction is conducted. Firstly, the feed aldehydes may be directly hydrogenated to the alcohol. Secondly, the feed aldehyde may undergo an aldol condensation in the basic medium and primary amine which has already been formed can react with the feed aldehyde via the azomethine intermediate to form a secondary amine which can then further react in a similar fashion to form a tertiary amine. Moreover, the aldol condensation products contain reactive groups which together with the nitrogen-containing compounds can form comparatively high-boiling condensation products. To improve selectivity in the direction of the primary aliphatic amines and to suppress the formation of high-boiling by-products, various measures have been proposed in the prior art, for example using excess ammonia or a solvent when it is likely that the reaction mixture will become inhomogeneous as a result of the water formed (Houben-Weyl, Methoden der organischen Chemie, 4th edition, Georg Thieme Verlag Stuttgart, Volume XI/1, p. 602 ff.).

DE 936211 describes a liquid-phase process for preparing primary aliphatic amines. In this process, the aldehyde to be reacted is first mixed with ammonia at temperatures below 0° C. Optionally, the aldehydes are diluted with a low-boiling alcohol, for example methanol. This mixture is then catalytically hydrogenated, for example over a cobalt or nickel catalyst, at elevated temperature and pressure in the liquid-phase mode or trickle mode.

According to DE 199 35 448 A1, a mixture of methanol and ammonia is admixed with Raney nickel and, following pressurization with hydrogen, is heated to reaction temperature. The aldehyde is then added. After completion of the reaction, the batch is depressurized and methanol and ammonia evaporate. The primary aliphatic amine which remains is then further reacted.

DE 10 2010 045 142 A1 discloses a solvent-free process in the liquid phase in which the feed aldehyde is reacted with hydrogen and ammonia in the presence of a hydrogenation catalyst at a temperature of 100 to 170° C. and a pressure of 6 to 11 MPa and wherein at least 30 mol of ammonia are used per mole of feed aldehyde.

The prior art also refers to using ammonia under supercritical conditions in the reductive amination process. The critical temperature of ammonia is 132.5° C. and the critical pressure is 112.5 atm (Handbook of Chemistry and Physics, 50$^{th}$ Edition 1969, The Chemical Rubben CO, p. F-64), corresponding to 11.4 MPa. According to GB 1,421,278, the reaction temperature is limited to 160° C. and the superatmospheric pressure up to 125 atm (corresponding to 12.7 MPa). In a preferred embodiment, the molar ratio of ammonia to feed aldehyde is restricted to 16 to 1. Working example 4 in GB 1,421,278 discloses the reductive amination of isobutyraldehyde with ammonia at a reaction temperature of 140° C. and a superatmospheric pressure of 125 atm (12.7 MPa superatmospheric pressure).

According to WO97/38955 A1, the reductive amination of aldehydes is carried out in a continuous process in the presence of a heterogeneous catalyst, wherein at least one reaction partner, in addition to hydrogen, is in the supercritical state or close to the supercritical state. The reaction is preferably conducted in the presence of a solvent, which is itself present in the supercritical state under the reaction conditions, such that hydrogen and the other reaction components are present in a homogeneous phase. It cannot generally be deduced from the prior art that aliphatic aldehydes having a mid-range carbon number are converted with high selectivity to primary aliphatic amines under conditions above the critical conditions for ammonia. The formation of high-boiling by-products is frequently observed which decreases the selectivity and thereby the yield of the desired primary aliphatic amine. In addition, the methods according to the prior art are prone to only a limited catalyst service life, whereby, besides the decreased yield of the desired amine mentioned, economic disadvantages are also associated with the amination process.

It is therefore an object of the present invention to provide a process for preparing primary aliphatic amines which is technically simple and in which the desired primary aliphatic amines are obtained with high selectivity. In particular, the formation of high-boiling by-products should be suppressed as far as possible. At the same time the service life of the hydrogenation catalyst should also be extended.

SUMMARY OF INVENTION

The present invention therefore provides a continuous process for preparing primary aliphatic amines having 3 to 18 carbon atoms by reacting corresponding aliphatic aldehydes with ammonia and hydrogen in the presence of a hydrogenation catalyst. The process is characterized in that the reaction is carried out without solvent at a molar ratio of aliphatic aldehyde to ammonia of more than 1 to 16, above the critical temperature and above the critical pressure of ammonia.

Surprisingly, in the solvent-free procedure with supercritical ammonia, the formation of selectivity-reducing high boilers can be supressed to below 10% by weight in the reaction product when specific settings are used for the reaction conditions in the continuous process. A further unexpected advantage of the process according to the invention is the extension of the catalyst service life when ammonia is reacted above its critical point. Separate pre-mixing of the ammonia and aliphatic aldehyde feeds with cooling is not required. The feed materials are fed separately but concurrently into the amination reactor directly from their reservoir vessels without further apparatus measures.

BRIEF DESCRIPTION OF DRAWINGS

The invention is described in detail below with reference to FIG. 1 which is a schematic diagram illustrating the process of the invention.

DETAILED DESCRIPTION

In the context of the present invention, the term solvent-free is understood to mean that the active addition of a solvent or diluent is dispensed with. However, small amounts of secondary constituents can be present in the feed materials, for example residual alcohol in the feed aldehydes which is left over from their preparation process and has solvent or diluent properties. Nor is the water formed during the reaction covered by the term solvent or diluent, even though it acts like a solvent in relation to ammonia.

More than 16 mol of ammonia, preferably at least 18 mol of ammonia and particularly at least 20 mol of ammonia are used per mole of aliphatic aldehyde. Although the large excess of ammonia leads to a dilution effect and thereby counteracts the formation of high boilers, the high proportion of the basic compound should ensure nonetheless that the aldehyde condensation proceeds to an appreciable extent, particularly since no added solvent or diluent is present according to the procedure of the present invention. Despite a large ammonia excess, the formation of high-boiling condensation products can surprisingly be suppressed provided the reductive amination is carried out above the critical temperature and above the critical pressure for ammonia. In order to achieve economically viable yields of primary aliphatic amines it is essential to use more than 16 mol of ammonia per mole of aliphatic aldehyde. An upper limit for the ammonia excess is not critical and is defined only by methodological or economic considerations. In a preferred embodiment of the invention the molar ratio of aliphatic aldehyde to ammonia is 1 to 18 to 1 to 60, preferably 1 to 20 to 1 to 50.

The reaction of aliphatic aldehyde with ammonia in the presence of hydrogen over the hydrogenation catalyst is conducted above the critical conditions for ammonia, in particular at temperatures above 132.5° C. to 190° C., preferably above 132.5° C. to 180° C. and especially preferably at temperatures above 160° C. to 180° C. The reaction pressure, which is the total pressure, is preferably adjusted to above 11.4 MPa, the critical pressure of ammonia, up to 20 MPa, particularly above 12.8 to 20 MPa. Very particularly, a reaction pressure of 13 to 18 MPa is established.

The hydrogenation catalysts used are customary catalysts used in the reductive amination of carbonyl compounds and contain at least one metal of transition groups 8 to 11 of the Periodic Table, such as nickel, cobalt, platinum, palladium, iron, rhodium or copper. Nickel or cobalt catalysts are particularly preferred. In addition to unsupported catalysts, such as Raney nickel or Raney cobalt, it is also possible to use supported catalysts. Supported catalysts generally contain the catalytically active metal in an amount of approximately 5% to 70% by weight, preferably approximately 10% to approximately 65% by weight and more particularly approximately 20% to 60% by weight, in each case based on the total weight of the hydrogenation catalyst. Suitable catalyst supports are any conventional support materials, for example aluminium oxide, aluminium oxide hydrates in their various forms, silicon dioxide, polysilicic acids (silica gels) including kieselguhr, silica xerogels, magnesium oxide, zinc oxide, zirconium oxide and activated carbon. In addition to the main components, catalytically active metal and support material, the hydrogenation catalysts may further contain minor amounts of additives used, for example, to improve their hydrogenation activity and/or their service life and/or their selectivity. Additives of this type are known; they include for example the oxides of calcium, of barium, of zinc, of aluminium, of zirconium and of chromium. They are generally added to the hydrogenation catalyst in a proportion of altogether 0.1% to 30% by weight, based on the total weight of the hydrogenation catalyst. Nickel has proved to be the preferred catalytically active metal. More particularly, nickel catalysts on kieselguhr as support material with chromium as additive are suitable for the amination process of the present invention. Nickel catalysts containing 20% to 60% by weight of nickel, from 20% to 70% by weight of kieselguhr and from 10% to 20% by weight of chromium, in each case based on the total weight of the hydrogenation catalyst and optionally fillers making up the balance to 100% by weight, are very particularly suitable.

The reductive amination is carried out, for example, on fixed-bed catalysts according to the trickle mode or liquid-phase mode and also the fluidized bed process. In addition to hydrogen, aliphatic aldehyde and ammonia are fed separately but concurrently into the amination reactor from their reservoir vessels.

The continuous reductive amination is preferably carried out in a tubular reactor over fixed-bed hydrogenation catalysts. A tubular reactor is also understood to mean a bundle of several tubes connected closely in parallel. The tubular reactors used may also comprise random packings or internals, for example Raschig rings, saddles, Pall rings, filter plates or column trays and also optionally stirring devices. In a particularly preferred configuration, the reductive amination is carried out in a tubular reactor but without internals with agitated hydrogenation catalyst.

In the continuous mode, a catalyst hourly space velocity V/Vh of aliphatic aldehyde, expressed in throughput volume of aliphatic aldehyde per unit catalyst volume and time, of 0.02-1.00 $h^{-1}$, preferably 0.10-0.80 $h^{-1}$, has proven to be advantageous. A higher loading of hydrogenation catalyst with aliphatic aldehyde is to be avoided, since the reductive amination no longer goes to completion and, due to the high aldehyde residue content, an increased formation of high-boiling by-products is observed.

With excessively low throughput per unit time, the plant capacity is not fully utilized.

In addition to ammonia as starting compound, the reductive amination is preferably conducted with pure hydrogen. However, besides pure hydrogen, mixtures may also be used comprising free hydrogen and, in addition, constituents inert under the conditions of the reductive amination.

The aliphatic aldehydes to be reacted by the process according to the invention contain 3 to 18 carbon atoms in the molecule, preferably 5 to 15 and especially preferably 8 to 15. The source of the aliphatic aldehydes is not limited to particular preparation methods.

Owing to their ready availability, aldehydes are preferably obtained by the oxo process or hydroformylation, i.e. by reacting the corresponding olefins having one less carbon atom with carbon monoxide and hydrogen, while both straight-chain and branched olefins and also alicyclic olefins, for example dicyclopentadiene or olefin oligomers such as tripropylene or tetrapropylene, may be used as starting materials for the hydroformylation reaction. Suitable aliphatic aldehydes are both straight-chain n- and branched-chain iso-aldehydes and also alicyclic aldehydes either in pure form or as a mixtures with isomeric aldehydes of the same carbon number. Mixtures of aliphatic aldehydes having different numbers of carbon atoms may also be used. The process of the present invention is particularly useful for converting aliphatic aldehydes having 8 to 15 carbon atoms to the corresponding primary aliphatic amines, for example 2-ethylhexanal, octanal, nonanal, decanal, undecanal, dodecanal, tridecanal, tetradecanal or pentadecanal or mixtures thereof. The corresponding aldehydes may be used as straight-chain compounds, as branched structural isomers or as a mixture of straight-chain and branched structural isomers, even with different carbon numbers. The mixture of straight-chain n- and branched iso-aldehydes containing 13 and 15 carbon atoms in the molecule is especially suitable for the amination process according to the invention. The preparation of 3(4), 8(9)-bis (aminomethyl)tricyclo[5.2.1.0$^{2,6}$]decane by the reductive amination of 3(4),8(9)-bisformyltricyclo[5.2.1.0$^{2,6}$]decane may also be carried out by the procedure according to the invention.

The reaction mixture removed from the amination reactor is passed into a high-pressure separator where a gaseous and a liquid phase are formed. The gaseous phase essentially contains ammonia and hydrogen and also small amounts of water of reaction and is removed. The liquid phase obtained is depressurized to atmospheric pressure via a level controller and flows into a reservoir vessel. During the depressurization process, ammonia and hydrogen dissolved in the liquid phase come out of the liquid phase and are removed from the reservoir vessel as depressurization off-gas. Ammonia can be recovered from the removed off-gas of the high-pressure separator and from the depressurization off-gas, and fed back into the reductive amination process.

Residual amounts of ammonia and the water of reaction are subsequently removed from the liquid phase collected in the reservoir vessel. The primary aliphatic amine obtained is subsequently purified in a conventional manner, by distillation for example, to form on-spec product.

The occasionally observed catalyst ageing effects during continuous operation, which generally manifest as an increase in the high-boiling fraction, may be counteracted by an increase in the reaction temperature during the continuous process, for example starting from above 132.5° C. up to 190° C. The service life of the hydrogenation catalyst can thereby be extended.

The process according to the present invention converts aliphatic aldehydes at high conversion and selectivity into the corresponding primary aliphatic amines. The level of high-boiling by-products, as determined by gas chromatography, in the crude product obtained after removal of ammonia and water of reaction formed is below 10%.

The process of the present invention will be more particularly elucidated below with reference to the in-principle scheme of FIG. 1. However, the process of the present invention is not restricted to the embodiment depicted in the drawing.

Line (1) introduces ammonia, line (2) hydrogen and line (3) aliphatic aldehyde in a continuous manner into the amination reactor (4) packed with the hydrogenation catalyst, which is operated above the critical conditions for ammonia. The reactor effluent exits via line (5) into a high-pressure separator (6) where a gaseous phase and liquid phase are formed. The gas phase from the high-pressure separator (6) is removed via line (7). Ammonia is recovered from the removed gas phase, which consists essentially of ammonia and hydrogen and contains small amounts of water of reaction, and is returned (not shown in FIG. 1) back into the process via line (1). The liquid phase obtained in the high-pressure separator (6) is removed via line (8), depressurized to atmospheric pressure via a level controller (9) and passes via line (10) at atmospheric pressure into the reservoir vessel (11). The gaseous fractions formed in the course of the depressurizing operation, which are essentially residual amounts of dissolved ammonia and hydrogen, are removed from the system via line (12). Optionally, ammonia can be recovered from the removed stream and returned (not shown in FIG. 1) back into the amination reactor (4) via line (1) together with fresh ammonia. The devolatilized liquid phase is removed via line (13) and subsequently worked up by distillation in a conventional manner (not shown in FIG. 1).

The process of the present invention will be more particularly elucidated below with reference to some examples.

Experimental Set-Up

The reductive amination was carried out over a commercial kieselguhr-supported nickel catalyst with chromium as additive in a tubular reactor in the liquid-phase mode. The aliphatic aldehyde used was a mixture of straight-chain n- and branched-chain iso-$C_{13}$ and $C_{15}$ aldehydes. Feed aldehyde, ammonia and hydrogen were fed separately but concurrently to the bottom end of the tubular reactor in a continuous manner. The reaction product was withdrawn at the top of the tubular reactor and passed into a high-pressure separator. The generated liquid was depressurized to atmospheric pressure via a level controller and passed into an atmospheric reservoir vessel. The organic crude product obtained was subsequently analysed by gas chromatography.

The reaction conditions and the continuous feed of the starting materials were set in accordance with the conditions of Tables 1, 2 and 3 below.

The Tables also report the composition of the organic product, without ammonia and water, determined by gas chromatography (area %).

The aliphatic aldehyde mixture used for the experiments in Tables 1-3 had the following typical composition (determined by gas chromatography, reported in area percent):

| | |
|---|---|
| $C_{12}$ and $C_{14}$ HC | 2.1 |
| n-/i-$C_{13}$ aldehyde | 62.5 |
| n-/i-$C_{15}$ aldehyde | 34.9 |
| After-run C26-C30 | 0.5 |

TABLE 1

Reductive amination of an n-/iso-$C_{13}/C_{15}$ aldehyde mixture and gas chromatographic analyses of resulting crude primary aliphatic amine in area % (without ammonia and water)

|  | Example 1 (Comparative; Example 4 from GB 1,421,278) | Example 2 (Comparative; Data from Claim 4 of GB 1,421,278) | Example 3 | Example 4 |
|---|---|---|---|---|
| Catalyst amount [ml] | 1950 | 1950 | 1950 | 1950 |
| Pressure [MPa], total | 12.7 | 12.7 | 13.0 | 13.0 |
| Catalyst temperature [° C.] | 140 | 140 | 140 | 140 |
| Hydrogen feed [g/h] | 30 | 30 | 31 | 30 |
| Aldehyde feed [g/h] | 402 | 402 | 401 | 400 |
| Ammonia feed [g/h] | 130 | 520 | 800 | 1500 |
| V/Vh based on aldehyde [1/h] | 0.25 | 0.25 | 0.25 | 0.25 |
| Molar ratio aldehyde/ammonia | 1:4 | 1:16 | 1:25 | 1:47 |
| Product analysis |  |  |  |  |
| Pre-run | 0.1 | 2.9 | 0.6 | 0.2 |
| $C_{12}$ and $C_{14}$ HC | 2.1 | 2.4 | 1.8 | 1.9 |
| Alcohols | 0.1 | 0.5 | 0.4 | 0.7 |
| Nitriles | 0.1 | 0.3 | 0.1 | 0.1 |
| n/i-$C_{13}$ amine | 2.3 | 53.6 | 62.7 | 62.1 |
| n/i-$C_{15}$ amine | 1.2 | 24.4 | 31.7 | 33.1 |
| Higher boilers | 94.1 | 15.9 | 2.7 | 1.9 |
| Total | 100.00 | 100.00 | 100.00 | 100.00 |

The comparative examples 1 and 2 show the results of reductive amination of an n-/iso-$C_{13}/C_{15}$ aldehyde mixture under conditions described as suitable in GB1,421,278. The extensive formation of high-boilers is evident when using conditions known from the prior art. According to inventive examples 3 and 4 on the other hand, when the molar ratio of ammonia to aldehyde is increased above that recommended in GB 1,421,278, the high-boiler formation can be decreased to an unexpectedly significant extent.

In comparison to comparative example 5, the reaction temperature in comparative example 6 was raised to the upper limit specified in Claim 1 of GB 1,421,278. In both examples, using the reaction settings recommended in the prior art, distinct, economically non-viable high-boiler formation is observed.

When the reaction settings 7-11 are used in accordance with the invention, using a higher molar ratio of ammonia to aldehyde, the high-boiler formation can be reduced, the more

TABLE 2

Reductive amination of an n-/iso-$C_{13}/C_{15}$ aldehyde mixture and gas chromatographic analyses of resulting crude primary aliphatic amine in area % (without ammonia and water)

|  | Example 5 (Comparative) | Example 6 (Comparative) | Example 7 | Example 8 | Example 9 | Example 10 | Example 11 |
|---|---|---|---|---|---|---|---|
| Catalyst amount [ml] | 1950 | 1950 | 1950 | 1950 | 1950 | 1950 | 1950 |
| Pressure [MPa], total | 12.7 | 12.7 | 13.0 | 13.0 | 13.0 | 13.0 | 16.0 |
| Catalyst temperature [° C.] | 140 | 160 | 140 | 150 | 170 | 180 | 180 |
| Hydrogen feed [g/h] | 30 | 30 | 30 | 29 | 30 | 30 | 30 |
| Aldehyde feed [g/h] | 900 | 902 | 900 | 900 | 901 | 900 | 900 |
| Ammonia feed [g/h] | 1140 | 1140 | 1500 | 1500 | 1500 | 1500 | 1500 |
| V/Vh based on aldehyde [1/h] | 0.56 | 0.56 | 0.56 | 0.56 | 0.56 | 0.56 | 0.56 |
| Molar ratio aldehyde/ammonia | 1:16 | 1:16 | 1:21 | 1:21 | 1:21 | 1:21 | 1:21 |
| Product analysis |  |  |  |  |  |  |  |
| Pre-run | 0.0 | 0.0 | 0.0 | 0.1 | 0.0 | 0.0 | 0.0 |
| $C_{12}$ and $C_{14}$ HC | 1.7 | 1.9 | 1.8 | 1.8 | 1.9 | 2.0 | 2.0 |
| Alcohols | 0.2 | 0.2 | 0.2 | 0.1 | 0.2 | 0.2 | 0.3 |
| Nitriles | 0.1 | 0.1 | 0.1 | 0.1 | 0.1 | 0.1 | 0.1 |
| n/i-$C_{13}$ amine | 3.1 | 45.4 | 54.6 | 62.0 | 62.7 | 62.4 | 62.9 |
| n/i-$C_{15}$ amine | 0.5 | 21.2 | 26.1 | 32.9 | 33.5 | 33.9 | 33.6 |
| Higher boilers | 94.4 | 31.2 | 17.2 | 3.0 | 1.6 | 1.4 | 1.1 |
| Total | 100.00 | 100.00 | 100.00 | 100.00 | 100.00 | 100.00 | 100.00 |

Comparative example 5 was carried out according to the conditions of comparative example 1 with the exception that the catalyst hourly space velocity was raised to 0.56 h$^{-1}$, a value in the region of which is recorded also in GB 1,421,278.

significantly the higher the reaction temperature (examples 7-10). When the pressure according to example 11 compared to example 10 is raised from 13 to 16 MPa, the high-boiler formation can be further reduced.

TABLE 3

Reductive amination of an n-/iso-$C_{13}/C_{15}$ aldehyde mixture and gas chromatographic analyses of resulting crude primary aliphatic amine in area % (without ammonia and water)

|  | Example 7 (from Table 2) | Example 12 | Example 13 | Example 14 |
|---|---|---|---|---|
| Catalyst amount [ml] | 1950 | 1950 | 1950 | 1950 |
| Run time [h] | 212 | 1708 | 1751 | 1847 |
| Pressure [MPa], total | 13.0 | 13.0 | 13.0 | 13.0 |
| Catalyst temperature [° C.] | 140 | 140 | 170 | 180 |
| Hydrogen feed [g/h] | 30 | 30 | 30 | 30 |
| Aldehyde feed [g/h] | 900 | 900 | 901 | 900 |
| Ammonia feed [g/h] | 1500 | 1500 | 1500 | 1500 |
| V/Vh based on aldehyde [1/h] | 0.56 | 0.56 | 0.56 | 0.56 |
| Molar ratio aldehyde/ammonia | 1:21 | 1:21 | 1:21 | 1:21 |
| Product analysis |  |  |  |  |
| Pre-run | 0.0 | 0.0 | 0.0 | 0.0 |
| $C_{12}$ and $C_{14}$ HC | 1.8 | 2.0 | 1.9 | 2.1 |
| Alcohols | 0.2 | 0.2 | 0.2 | 0.2 |
| Nitriles | 0.1 | 0.1 | 0.1 | 0.1 |
| n/i-$C_{13}$ amine | 54.6 | 34.6 | 62.1 | 62.6 |
| n/i-$C_{15}$ amine | 26.1 | 15.0 | 33.6 | 33.2 |
| Higher boilers | 17.2 | 48.1 | 2.1 | 1.8 |
| Total | 100.00 | 100.00 | 100.00 | 100.00 |

The conditions according to the invention also make it possible to compensate for the ageing effects of the fixed-bed catalyst. Example 7 shows the hydrogenation catalyst characteristics following a run time of 212 h. A distinct increase in high-boilers due to ageing of the catalyst is observed following a total running time of 1708 h (example 12). As shown in examples 13 and 14, the ageing effect of the hydrogenation catalyst can be counteracted if the reaction temperature is increased to a region beyond the temperature region recommended in GB 1,421,278. By a temperature increase over the run time, the ageing effect of the catalyst can be compensated for and in this manner the high-boiler formation is reduced and the preparation of primary $C_{13/15}$ amines is conducted in a sustainable economic manner.

The invention claimed is:

1. Continuous process for preparing primary aliphatic amines having 3 to 18 carbon atoms by reacting corresponding aliphatic aldehydes with ammonia and hydrogen in the presence of a hydrogenation catalyst, characterized in that the reaction is carried out without solvent at a molar ratio of aliphatic aldehyde to ammonia of more than 1 to 16, above the critical temperature and above the critical pressure of ammonia.

2. Process according to claim 1, characterized in that the molar ratio of aliphatic aldehyde to ammonia is 1 to 18 or more.

3. Process according to claim 1, characterized in that the molar ratio of aliphatic aldehyde to ammonia is from 1 to 18 to 1 to 60.

4. Process according to claim 1, characterized in that the reaction is conducted at a temperature above 132.5° C. and up to an upper limit of 190° C.

5. Process according to claim 1, characterized in that the reaction is conducted at a pressure above 11.4 and up to an upper limit of 20 MPa.

6. Process according to claim 1, characterized in that the aliphatic aldehydes to be reacted contain 5 to 15 carbon atoms in the molecule.

7. Process according to claim 1, characterized in that the hydrogenation catalyst contains at least nickel, cobalt, platinum, palladium, iron, rhodium or copper.

8. Process according to claim 1, characterized in that the hydrogenation catalyst contains a support material.

9. Process according to claim 1, characterized in that the hydrogenation catalyst contains oxides of calcium, of barium, of zinc, of aluminium, of zirconium, of chromium or mixtures thereof, as additives.

10. Process according to claim 1, characterized in that the hydrogenation catalyst used is a nickel catalyst containing 20% to 60% by weight of nickel, from 20% to 70% by weight of kieselguhr and from 10% to 20% by weight of chromium, in each case based on the total weight of the hydrogenation catalyst and optionally fillers making up the balance to 100% by weight.

11. Process according to claim 1, characterized in that the aliphatic aldehydes to be reacted are used as a mixture of aliphatic aldehydes having different numbers of carbon atoms.

12. Process according to claim 1, characterized in that a mixture of straight-chain n- and branched-chain iso-aldehydes containing 13 and 15 carbon atoms in the molecule is used.

13. Process according to claim 1, characterized in that the aliphatic aldehyde 3(4),8(9)-bisformyltricyclo[$5.2.1.0^{2,6}$]decane is reacted.

14. Process according to claim 1, characterized in that the molar ratio of aliphatic aldehyde to ammonia is 1 to 20 or more.

15. Process according to claim 14, characterized in that the molar ratio of aliphatic aldehyhde to ammonia is from 1 to 20 to 1 to 50.

16. Process according to claim 1, characterized in that the reaction is conducted at a temperature above 132.5° C. and up to an upper limit of 180° C.

17. Process according to claim 16, characterized in that the reaction is conducted at a temperature above 160° C. and up to an upper limit of 180° C.

18. Process according to claim 1, characterized in that the reaction is conducted at a pressure above 12.8 MPa and up to an upper limit of 20 MPa.

19. Process according to claim 1, characterized in that the reaction is conducted at a pressure of from 13 to 18 MPa.

20. Process according to claim 1, characterized in that the aliphatic aldehydes to be reacted contain from 8 to 15 carbon atoms in the molecule.

\* \* \* \* \*